United States Patent [19]

Takagi et al.

[11] Patent Number: 4,770,542

[45] Date of Patent: Sep. 13, 1988

[54] PROCESS FOR THE ACCELERATION OF PHOTODEGRADATION OF POLYMER SUBSTANCES

[75] Inventors: Akio Takagi, Tokyo; Hiroyuki Higuchi, Kanagawa; Yoshihito Ohtake, Tochigi; Hiroshi Matsunaka, Ibaragi, all of Japan

[73] Assignee: The Coca-Cola Company, Atlanta, Ga.

[21] Appl. No.: 872,495

[22] Filed: Jun. 10, 1986

[30] Foreign Application Priority Data

Jun. 10, 1985 [JP] Japan .............................. 124316/85

[51] Int. Cl.⁴ .................................................. G01K 17/00
[52] U.S. Cl. .................................... 374/57; 73/150 R
[58] Field of Search .............................. 374/14, 57, 53; 73/150 R, 865.6; 250/492.1

[56] References Cited

U.S. PATENT DOCUMENTS

| | | |
|---|---|---|
| 3,224,266 | 12/1965 | Klippert ............................ 73/150 R |
| 3,426,590 | 2/1969 | Suga ................................... 73/150 R |
| 3,488,681 | 1/1970 | Mita et al. ............................... 374/57 |
| 3,501,942 | 3/1970 | Fitzgerald et al. ..................... 374/57 |
| 3,636,348 | 1/1972 | Guillory et al. ................... 73/150 R |
| 3,664,188 | 5/1972 | Kockott ............................ 73/150 R |
| 3,675,477 | 7/1972 | Allen ................................. 73/150 R |
| 3,983,742 | 10/1976 | Suga ..................................... 374/57 |
| 4,012,954 | 3/1977 | Klippert ............................ 73/150 R |
| 4,544,995 | 10/1985 | Suga ................................... 73/865.6 |
| 4,627,287 | 12/1986 | Suga ....................................... 73/159 |

FOREIGN PATENT DOCUMENTS

| | | | |
|---|---|---|---|
| 0014740 | 1/1982 | Japan ................................ 73/865.6 |
| 0211528 | 12/1982 | Japan ................................ 73/865.6 |
| 0117128 | 6/1985 | Japan ..................................... 374/57 |
| 1226956 | 3/1971 | United Kingdom ............... 73/865.6 |

OTHER PUBLICATIONS

Bamford C. H. et al, "Polymer, The Chemistry, Physics and Technology of High Polymers", Butterworths Scientific Publications, London, 1965.

Doyle, C. D. "Estimating Thermal Stability of Experimental Polymers by Emperical Thermogravametric Analysis", Analytical Chemistry, vol. 33, No. 1, Jan. 1961, pp. 77–79.

Primary Examiner—William A. Cuchlinski, Jr.
Assistant Examiner—Thomas B. Will
Attorney, Agent, or Firm—Birch, Stewart, Kolasch & Birch

[57] ABSTRACT

A process and an apparatus for carrying out the process which causes acceleration of photodegradation of polymer substances. The process comprises irradiating a polymer substance with a low wavelength light and then a high wavelength light in an atmosphere with a specified humidity. The apparatus contains an irradiation lamp for irradiating a polymer substance, a rotating mounting plate for supporting the polymer substance, and humidifying means for creating a predetermined humidity for the photodegradation of the polymer substance. The photodegradation process and apparatus are used to precisely determine the useful life of polymer substances.

21 Claims, 11 Drawing Sheets

PROCESS FOR THE ACCELERATION OF PHOTODEGRADATION OF POLYMER SUBSTANCES

BACKGROUND OF THE INVENTION

1. Field of the Invention

The present invention relates to a process for the acceleration of photodegradation of polymer substances. More particularly, it relates to an effective process for the acceleration of photodegradation by which to precisely find the life of a polymer substance in the case where the polymer substance is used under usual conditions or the like.

2. Description of Related Art

In order to assess the light resistance of polymer substances, light resistant degradation test methods are currently employed using an artificial light source, such as a carbon arc lamp or a xenon lamp.

However, difficulty arises when attempting to precisely predict by these methods photodegradation of polymer substances in ordinary use conditions and this difficulty is experienced by and well known to many people. Usually, with regard to these methods conditions for the acceleration of degradation used to predict natural degradation, which are found by chance for a certain polymer substance, are not applicable at all for other polymer substances.

Therefore, because of the low reliability associated with the practice of accelerated degradation tests used to treat polymer substances under degradation-accelerated conditions to predict natural degradation, it was the usual practice to confirm the natural degradation and improve the reliability by carrying out outdoor exposure tests which require a long term.

SUMMARY OF THE INVENTION

The object of the present invention is to provide a process for the acceleration of photodegradation of polymer substances in order to simulate natural degradation of polymer substances.

Another object of the present invention is to provide a process for the acceleration of photodegradation of polymer substances which is capable of indicating natural degradation conditions by determining the conditions of a degraded polymer substance while at the same time being capable of easily providing the natural degradation conditions in a short period of time.

Still another object of the present invention is to provide a process for the acceleration of photodegradation which is adaptable to various polymer substances.

Further objects and advantages of the present invention will be clear from following explanations.

The present invention can achieve such objects and advantages by a process for the acceleration of photodegradation of polymer substances which comprises (1) irradiating a polymer substance with a first light having a bright line or continuous spectral peak with the maximum intensity in a wavelength region of 400 nm or less, and then (2) irradiating the polymer substance with a second light having a bright line or continuous spectral peak with the maximum intensity in a wavelength region exceeding 400 nm in an atmosphere with a water content of at least 0.034 g/l.

The features with the process of the present invention, as mentioned above, reside in step (1) irradiation with a first light and step (2) irradiation with a second light differing in wavelength from this first light.

It appears to be impossible to impart polymer substances with a desired reproducible photodegradation by reversing steps (1) and (2) or by simultaneous irradiation with a first light and a second light in a single step.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The first light used in step (1) of the present invention has a bright line or continuous spectral peak with the maximum intensity in a wavelength region of 400 nm or less, and the second light used in step (2) has a bright line or continuous spectral peak with the maximum intensity in a wavelength region exceeding 400 nm. Hereinafter the first light may be called the low wavelength light and the second light the high wavelength light according to the wavelength region in which the bright line or continuous spectral peak with the maximum intensity is present.

Another feature in the process of the present invention lies in carrying out the high wavelength light irradiation in step (2) in an atmosphere with a humidity corresponding to a water content of at least 0.034 g/l.

The low wavelength light used in the step (1) reaches as far as to the interior of the polymer substance to generate radicals or to create an excited condition. As a result, a crosslink reaction is caused and degradation is advanced. The high wavelength light used in step (2) accelerates crosslinking or degradation from the radicals formed in the excited condition created in step (1). In the case, however, where the irradiation in step (2) is not carried out in a proper humid atmosphere, it is impossible to impart the polymer substance with intended reproducible photodegradation.

The low wavelength used in step (1) can be obtained, for instance, from a low pressure mercury lamp, deuterium lamp or metal halide lamp. If a low pressure mercury lamp is chosen, it is preferably one which contains about 50 mmHg or less in mercury vapor pressure of enclosed mercury. The low pressure mercury lamp gives light having a strong bright line spectrum at 184 nm and 253.7 nm (maximum).

The low wavelength light is projected on the polymer substance and radicals are formed in the polymer substance or the polymer substance attains an excited condition. The low wavelength light irradiation is usually carried out in an ambient atmosphere. The temperature and humidity of the ambient atmosphere do not seriously affect the practice of step (1). Step (1) can be carried out, for instance, at a temperature of 0° to 80° C. and at a relative humidity of 0 to 100%.

The light irradiation time is varied according to the exposure dose. The exposure dose is varied according to the distance of the light source from the polymer substance. The dose of the low wavelength light can be set at about 30 to 100 milliwatts in bright line or peak with a wavelength of 250 nm per cm$^2$ of the surface area of the polymer substance. The dose should preferably be set at about 35 to 55 milliwatts on the same basis.

The dose rate of the low wavelength light should preferably be set at about 2.1 to 3.3 watts·minutes per $cm^2$ of the polymer substance.

The low wavelength light can be projected on the polymer substance for about 10 to about 120 minutes, for example. A suitable irradiation time may optionally be used carrying out preparatory tests, if need be, in the relation with the dose.

The light source of the low wavelength light can usually be located at a distance of about 100 cm or less from the polymer substance. Operationally this distance should preferably be set at about 20 to 250 cm.

The polymer substance irradiated with the low wavelength light in step (1) is then irradiated with the high wavelength light in step (2).

The high wavelength light used in step (2) can be obtained, for instance, from a high pressure or ultra-high pressure mercury lamp, xenon lamp, helium-cadmium laser or xenon flash lamp. Of these light sources, the high pressure or ultra-high pressure mercury lamp is preferably used. As a high pressure or ultra-high pressure mercury lamp, it is preferable to use one which is 1 to 20 atm. in mercury vapor pressure of enclosed mercury. The high pressure mercury lamp gives light having a strong bright line spectrum in 365 nm, 404 nm, 546 nm and 577 nm. Bright lines of 546 nm and 577 nm are the strongest.

The high wavelength light is projected on the polymer substance that has been irradiated with the low wavelength light in step (1). The high wavelength light irradiation should preferably be carried out immediately after the low wavelength light irradiation or after a brief interval that is within several hours.

The high wavelength light irradiation is carried out in an atmosphere with a water content of at least 0.034 g/l, such as in an atmosphere with a relative humidity of at least 67% at 40° C., and preferably in an atmosphere with a water content of at least 0.038 g/l.

The dose of the high wavelength light can be set at about 0.5 to 4 watts in bright line or peak with a wavelength of 420 nm per $cm^2$ of the surface area of the polymer substance. The dose should preferably be set at about 1 to 2 watts in bright line or peak with the wavelength of 420 nm on the same basis.

The dose rate of the high wavelength light should preferably be set at about 30 to 420 watts·minutes in bright line or peak with the wavelength of 420 nm per $cm^2$ of the polymer substance.

The high wavelength light can be projected on the polymer substance for about 10 to about 100 minutes, for instance, at the above dose. A suitable irradiation time may optionally be determined by carrying out preparatory tests, if need be, in the relation with the dose or the like.

The light source of the second light can be located at a distance of about 100 cm or less from the polymer substance. Operationally this distance should preferably be set at about 20 to about 50 cm.

Polymer substances contemplated as subject matter of the present invention may be, regardless of their kind, thermoplastic or setting polymers, elastic or non-elastic and addition, polyaddition or polycondensation polymers. Needless to say, the polymer substances may be homopolymers or copolymers.

Consequently, the present invention contemplates all known polymer substances as subject matter. There may be used, as subject matter, for instance, elastic addition polymers of ethylenic vinyl bond-containing monomers, such as ethylene, propylene, 1-butene, vinyl chloride, styrene and so on; elastic addition polymers of conjugated double bond-containing monomers, such as butadiene, chloroprene, isoprene, and so on; polyamides, such as polyhexamethyleneadipamide, poly-ε-caprolactam, polyhexamethylene sebacamide; polyesters, such as polyethylene terphthalate, polyethylene isophthalate and polytetramethylene terephthalate; polyurethanes, epoxy resins; polyesterethers, such as polyesterether (for instance, "Hytrel" (phonetic), a product of Du Pont Company) containing, as an acid component, terephthalic acid and as the main low molecular weight glycol component, ethylene glycol or tetramethylene glycol and as the main high molecular weight glycol component, polyethylene glycol or polytetramethylene glycol; polycarbonates, such as bisphenol A based polycarbonate and so on.

These polymer substances should conveniently be used in an appropriate size so as to be readily irradiated with light in the case of carrying out the process of the present invention for the acceleration of photodegradation. It will do to make a thin film, for instance, with a size on the order of 2 cm × 5 cm and about 5 mm or less, and further 1 mm or less, in thickness.

The instant inventors' study shows that the process of the present invention for the acceleration of photodegradation of polymer substances can produce a degraded condition in a very short period of time that is very similar to the degradation of polymer substances produced by natural conditions, such as polymer substances irradiated or not irradiated directly with sunlight indoors or outdoors in an ambient atmosphere. That is, the instant inventors' study shows that the degraded condition caused in polymer substances which are subjected to the process of the present invention for the acceleration of photodegradation can be precisely determined by the hereinbelow described thermogravimetric analytical method, whitening test and crack acceleration test. In addition, the present process simulates natural degradation.

Consequently, the present invention provides a process for the determination of the degradation life of polymer substances.

First, a polymer substance is subjected to the process of the present invention for the acceleration of photodegradation in order to prepare polymer substance samples which exhibit accelerated degradations with respect to a plurality of light wavelengths differing in irradiation time.

A plurality of samples prepared (which differ in high wavelength light irradiation time) are each subjected to the thermogravimetric analytical method to determine the relation between the proportion of heat weight loss and temperature (decomposition temperature) for the respective samples. It was empirically found from the results of many kinds of polymer substances that with respect to the proportion of weight loss falling in the range of below 5 weight % and over 95 weight %, the increase in weight loss due to the temperature rise is small, whereas with respect to the proportion of weight loss falling in the range of between 5 weight % and 95 weight %, the weight loss due to the temperature rise increases by a relatively great amount with good reproducibility.

In the case, consequently, where the proportion of weight loss is present between 5 weight % and 95 weight %, the decomposition temperature indicating that weight loss value can be specified with good reproducibility provided that the value is a predetermined weight loss value (value of 30% or 50%, for instance).

This decomposition temperature can be specified with better reproducibility in the case where the proportion of weight loss is present between 30 and 70 weight % and particularly with much better reproducibility as well as ease in the case where it is 50 weight %.

The respective samples are specified for their decomposition temperatures indicating predetermined weight loss values, and the relation of the decomposition temperature and the high wavelength light irradiation time of the polymer substance is determined by plotting the decomposition temperature on the ordinate for the respective samples and the high wavelength light irradiation time on the abscissa for the respective samples. Usually this relation indicates results in a curve with a peak. That is, it indicates that the decomposition temperature rises until the high wavelength light irradiation time reaches a peak, where upon if the high wavelength light irradiation time increases further, the decomposition temperature lowers. This is considered to indicate that until the peak of the curve is reached, crosslinking has the upper hand with respect to decomposition, whereas from that time on decomposition gains the upper hand over crosslinking upon irradiation of the high wavelength light.

In any case, the instant inventors' study shows that surprisingly enough, the relation of the decomposition temperature and the high wavelength light irradiation time determined from samples prepared by the process of the present invention agrees with or corresponds very well with the relation of the decomposition temperature (on the ordinate) and the use time (on the abscissa) of the same polymer substances which are continuously used in an ambient atmosphere. The scale of the use time in the latter relation is reduced at a fixed rate. This fact which was made clear for the first time by the instant inventors indicates that the degraded condition of polymer substances treated by the process of the present invention simulates the natural degradation condition of the same polymer substances.

The natural degradation of polymer substances usually results in a lowering of mechanical properties, such as strength, elongation, and surface scratching, cracking or changing of color, such as yellowing, whitening and so on.

In fact, in the determination of the relation between the decomposition temperature and the high wavelength light irradiation time, just as noted above with regard to natural degradation, there can be observed a lowering of mechanical properties, surface scratching, cracking or changing of color, such as yellowing, whitening and so on, in the polymer substances.

In general, the lowering of mechanic properties, surface scratching, cracking, whitening or the like in polymer substances occur during the irradiation period corresponding to the upper portion of the curve. Consequently, the peak of the curve has an important significance for the determination of the degradation life of polymer substances. Whitening usually begins at the peak or somewhat at the rear of the curve, and surface scratching or cracking occurs after whitening.

With respect to the relation of the decomposition temperature and the high wavelength light irradiation time it is easy to determine how many hours of actual use time of the polymer substance corresponds to high wavelength light irradiation time.

For example, the relation between the decomposition time and the high wavelength irradiation time according to the thermogravimetric method was determined for different samples. These samples were treated by the process of first irradiating the samples with a low wavelength for 40 minutes at a distance of 20 cm by means of a low pressure mercury lamp and then irradiating the samples with a high wavelength light by means of a high pressure mercury lamp in an atmosphere with a relative humidity of 85-90%. The decomposition temperature and irradiation time results were compared with the relation between the decomposition temperature and exposure time determined for the same polymer substances that had been exposed outdoors (at Yokohama). One hour of the high wavelength light irradiation time was found to correspond to nearly two months of the outdoor exposure time.

Further, it is noted that with respect to samples prepared by the process of first irradiating the sample with a low wavelength light for 90 minutes at a distance of 30 cm by means of low pressure mercury lamp and then irradiating the sample with a high wavelength light by means of high pressure mercury lamp in an atmosphere with a relative humidity of 85 to 90%, one hour of high wavelength light irradiation time is found to correspond to 1.1 to 1.2 months of outdoor exposure time.

The process of the present invention, as mentioned above, is applicable to various polymer substances. The polymer substances may contain a photostabilizer, such as an ultraviolet absorber, imparting resistance to photodegradation.

In order to product a degraded condition of a polymer substance containing a photostabilizer that is comparable to polymer substance not containing a photostabilizer it is sufficient to extend the high wavelength irradiation time until the photostabilizer is consumed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE DRAWINGS

Figure 1:
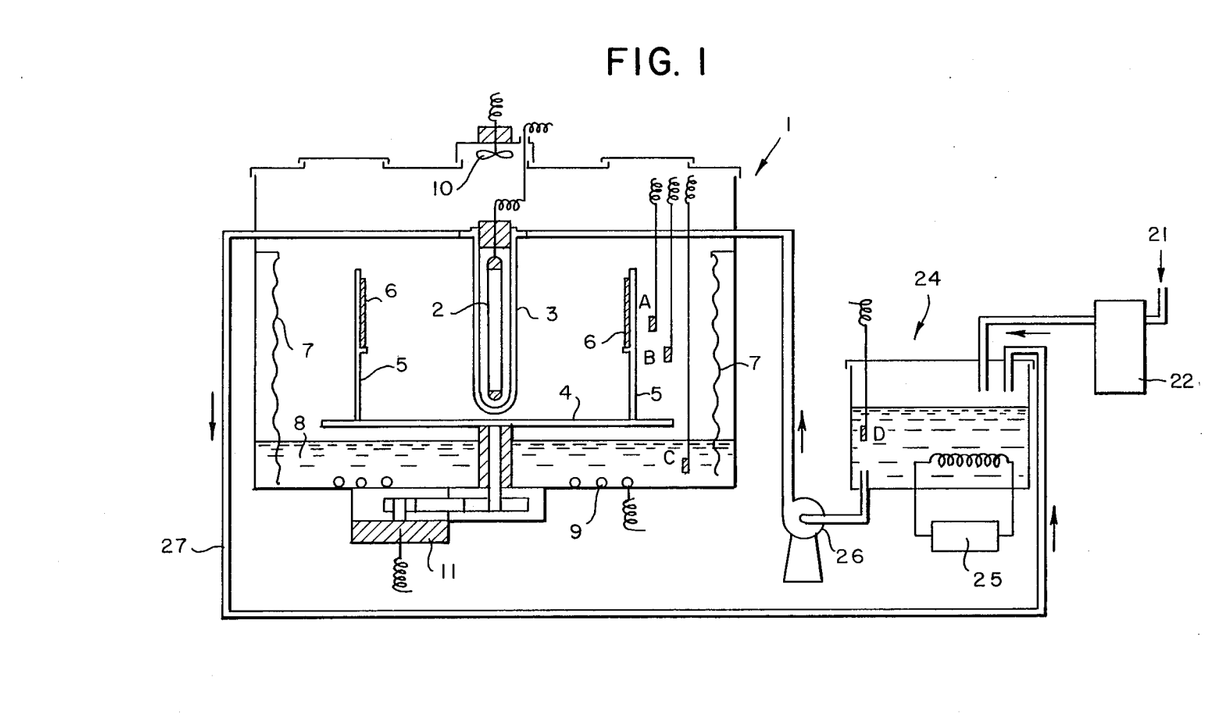
FIG. 1 is a schematic crossectional view showing one example of an apparatus used for the practice of the process of the present invention.

Experiments were conducted by the use of the apparatus shown in FIG. 1 of the accompanying diagrams.

In FIG. 1, the apparatus includes a photodegradation accelerator 1, an ultraviolet irradiation lamp 2, a lamp receiver composed of a jacket through which cooling water is passed 3, a rotary mounting plate 4, a sample support fixed on the rotary mounting plate 5, a sample 6, a humidifying cloth 7, water 8, a heater 9, an exhaust fan 10 and a drive motor 11 to rotate the mounting plate 4. Further A represents an illuminometer, B a hygrometer, and C and D are each thermometers.

During operation of the apparatus, tap water 21 passes through an ion exchanger 22 and proceeds to a cooler 24 where it is cooled by means of a refrigerator 25. The water then proceeds by means of a circulating pump 26 into the jacket of the lamp receiver 3 where it absorbs heat released from the lamp 2. It is then returned to the cooler 24 passing through a line 27.

Operation Procedures

In accordance with the procedure used for Examples 1-11, a polymer substance film 200±10 $\mu$m thick was prepared and scotch-taped to the sample support 5 so as to be stationary. The distance from the light source to the sample support was set at 30 cm. Upon engagement of the drive motor the mounting plate 4 was rotated (1 rpm) and the sample was rotated around the lamp.

The heater 9 was turned on and the water 8 was heated. The atmosphere within the photodegradation accelerator was adjusted in such a manner so as to reach a relative humidity of 85 to 90% at 42°±2° C. The water content of the atmosphere at that time is 0.043 to 0.046 g/l.

After the above preparation was made a low pressure mercury lamp was mounted as a light source (tradename ULO-6DQ, a product of Sen Tokushu Kogen K. K., having a bright line spectrum of 184 nm and 253.7 nm and used in combination with ULO-6AB, a stabilized power supply source made by the same company) and was first lighted for 40 minutes. After 40 minutes the low pressure mercury lamp was taken out from the lamp receiver 3 and in its place a high pressure mercury lamp (tradename UM-452, a product of Ushio Denki K. K., having a strong bright line spectrum of 365, 404, 546 and 577 nm, and used in combination with UM-453B-A, a stabilized power supply source made by the same company) was mounted. Cooling water was passed into the jacket of the lamp receiver and the high pressure mercury lamp was lighted for a predetermined period of time.

The polymer substance film irradiated by means of the high pressure mercury lamp was taken out from the apparatus at predetermined times and waterdrops on the surface were wiped off with gauze and dried at room temperature for 1 hour or more.

About a 4×4 mm square film (about 5 to 5.5 mg) was cut of from the dried film and analyzed by the thermogravimetric method. Analytical conditions of the thermogravimetric method are as follows:
Thermogravimetric analyzer: Suspension type TG-30 of Shimazu Seisakusho
Atmospheric gas and flow: Nitrogen gas, 40 ml/minute
Heating oven and temperature raising rate:
Mid-low temperature type, 10° C./minute
Sample container: Platinum
Chart speed: 10 mm/minute The polymer substance film having been irradiated by means of the high pressure mercury lamp was then immersed in a mixed solution of 1 volume part of 5 % aqueous sodium laurylsulfate solution and 9 volume parts of ½ N hydrochloric acid and treated for 30 minutes by heating at 80° C. After that, it was taken out and thoroughly washed with water and then air-dried. The air-dried product was observed with the unaided eye and it was found to be more whitened and unclear than the film untreated with light irradiation.

EXAMPLE 1

The film used was a film (200 $\mu$m thick) of the two liquid heat cure type polyether polyurethane (triol with molecular weight of about 3000 and diol with molecular weight of about 500 to 1000-based polyol/isophoronediisocyanate (IPDI) series).

Figure 2:
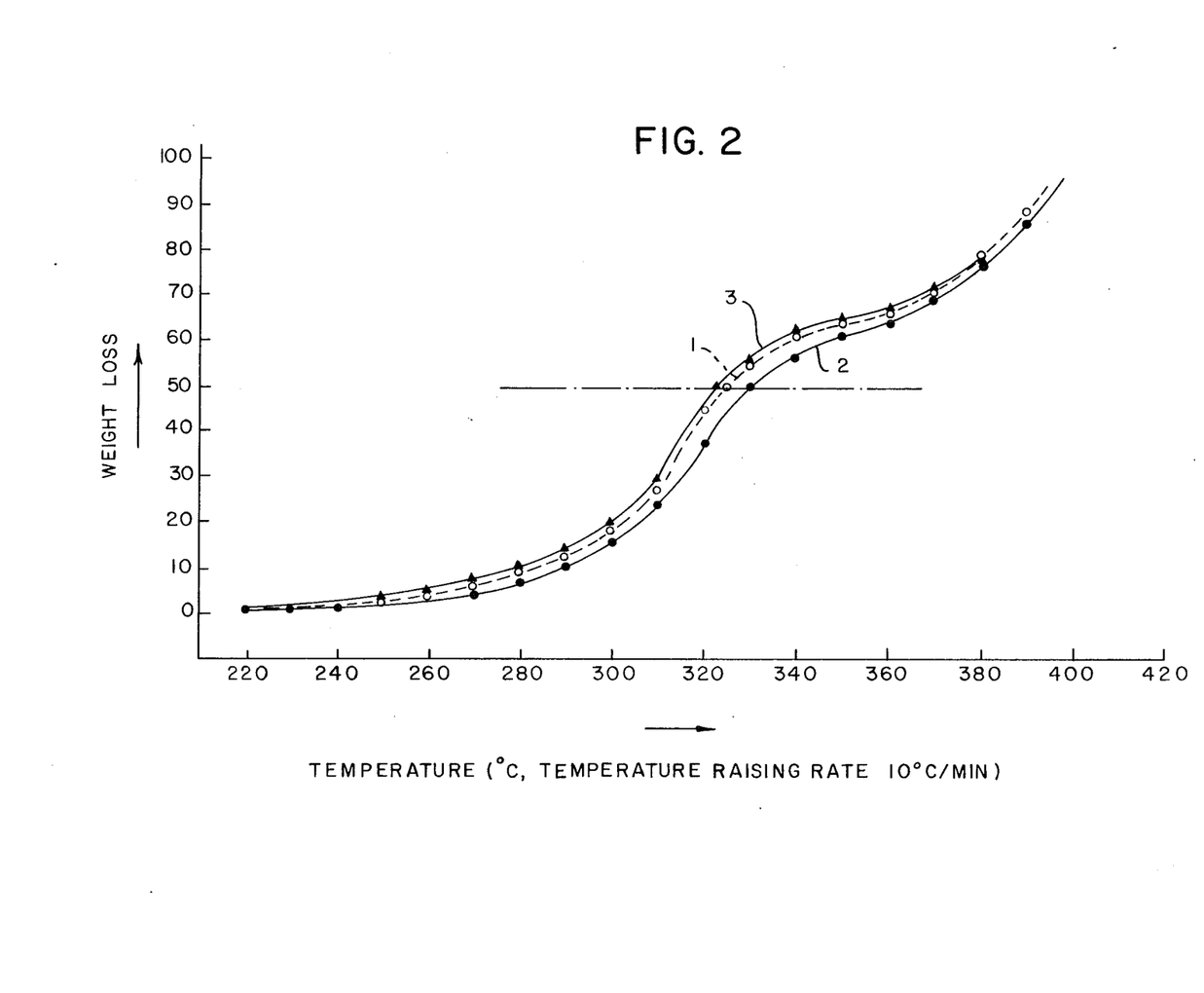
FIG. 2 indicates one example of the thermogravimetric analytical results (the relation of weight loss and temperature) of a polymer substance obtained by the practice of the process of the present invention.

Analytical results obtained by the thermogravimetric method are shown in FIG. 2.

In FIG. 2 curve 1 represents the film before the light irradiation and curves 2 and 3 represent the films after irradiation by the high pressure mercury lamp set at 360 minutes and 600 minutes, respectively.

Figure 3:
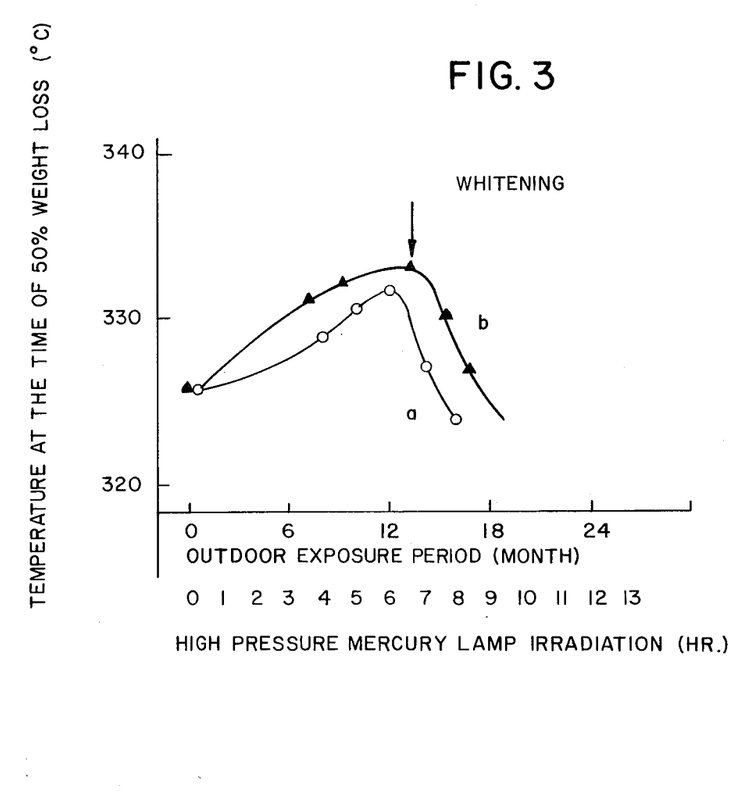
FIGS. 3-12 each indicate the relation of the high pressure mercury lamp irradiation time and the temperature upon 50% weight loss resulting from the thermogravimetric method according to the process of the present invention.

In FIG. 3 there are plotted temperatures at the time of 50% weight loss (on the ordinate) determined for the respective irradiation time by the high pressure mercury lamp (on the abscissa) from the curves of FIG. 2 and similar curves (curve a). It is noted that at the time when the film was irradiated for about 6 hours by means of a high pressure mercury lamp the temperature at the time of 50% weight loss is highest, whereas when the irradiation time is shorter or longer than that, said temperature is lower.

FIG. 3 indicates, as curve b, the relation obtained when the same film was exposed outdoors. The outdoor exposure data was obtained by placing the film out on the roof of Yokohama Plant of Japan Coca Cola Kabushiki Kaisha during the period of March 1982 through March 1984.

As FIG. 3 shows, by using a scale of 0.5 hours of high pressure mercury lamp irradiation time corresponding to 1 month of the outdoor exposure period the positions of curves a and b coincide well with each other.

EXAMPLE 2

The film used was a 2-layered film wherein the respective layers were formed of different polymer substances. One layer is a cured film (about 100 $\mu$m thick) of an epoxy resin from epichlorohydrin and bisphenol A containing an acid anhydride as a hardening agent, and the other layer is a thin layer (about 100 $\mu$m thick) of a styrene-butadiene rubber latex.

Light irradiation was conducted on the side of the epoxy resin.

Figure 4:
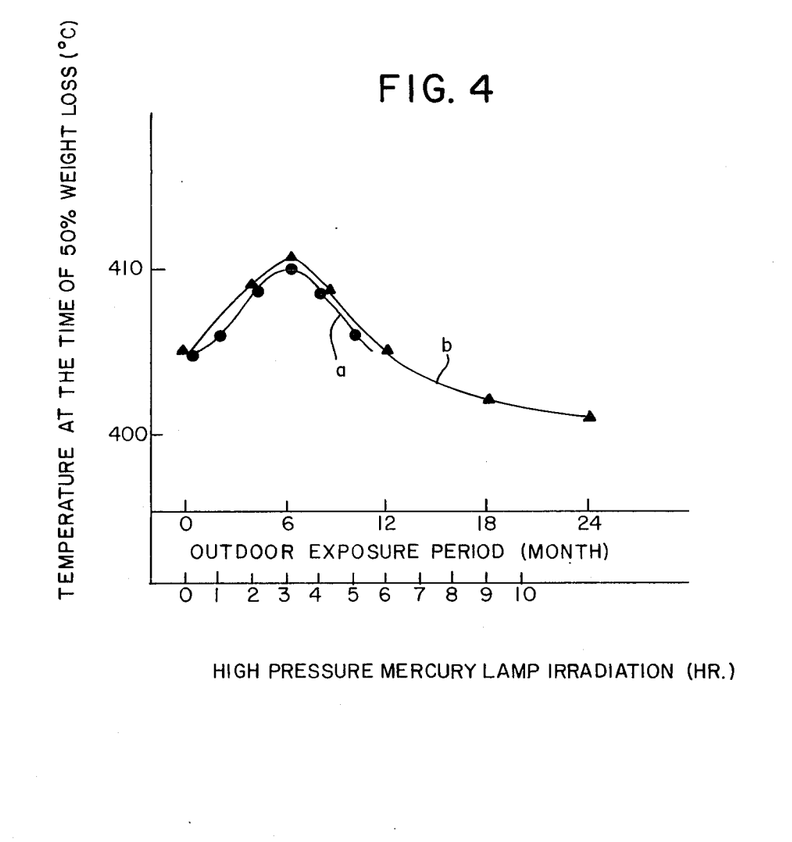

Results are shown in FIG. 4. In FIG. 4 as well, curve a is the result obtained in the case of irradiation by the high pressure mercury lamp, and curve b is the result obtained in the case of outdoor exposure. In FIG. 4 it is noted that 0.5 hours of the high pressure mercury lamp irradiation time corresponds to 1 month of the outdoor exposure period.

EXAMPLE 3

The film used was a film (about 200 $\mu$m thick) of polyester-polyether polyurethane (of the 2-liquid heat cure type).

Figure 5:
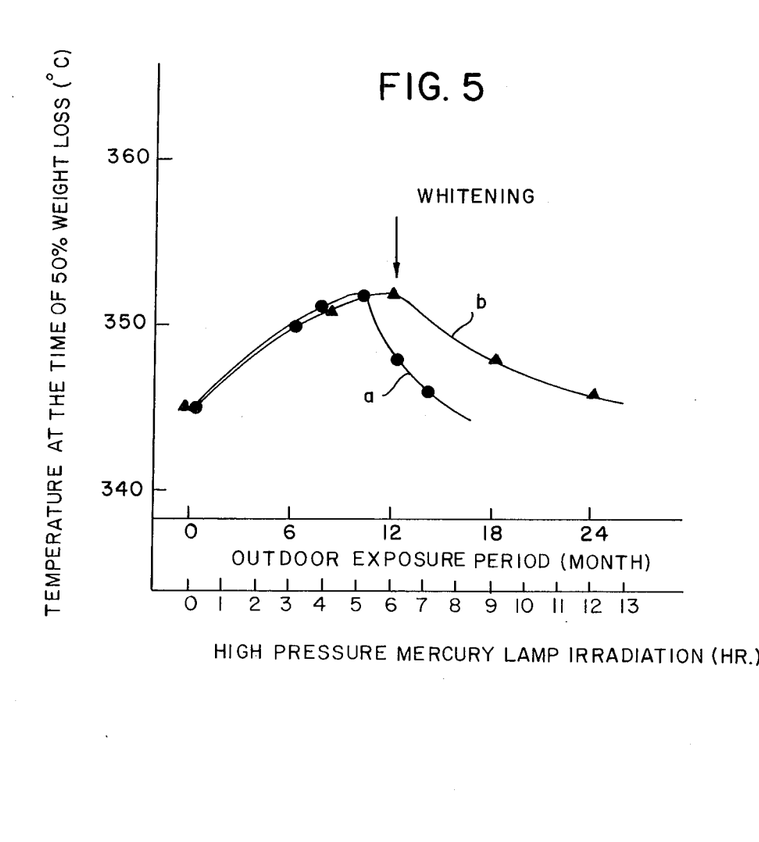

Results obtained are shown in FIG. 5. Again, curve a (irradiation by the high pressure mercury lamp) and curve b (outdoor exposure) correspond to each other.

EXAMPLE 4

The film used was a film about 200 $\mu$m thick prepared by the use of a polyether urethane (polypropylene glycol/IPDI, hydrogenated MDI) emulsion.

Figure 6:
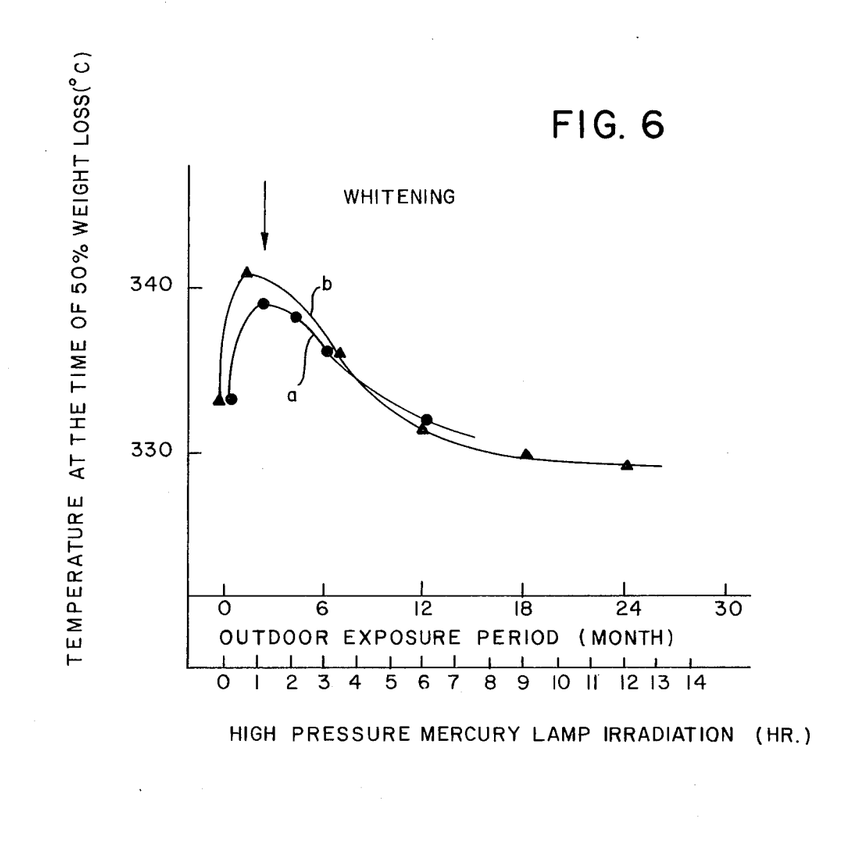

Results obtained are shown in FIG. 6. Curve a (irradiation by the high pressure mercury lamp) and curve b (outdoor exposure) correspond to each other.

EXAMPLE 5

The film used was a film (100 μm thick) of an epoxyurethanic resin based on an epichlorohydrin/bisphenol A type epoxy, trimethylolpropane triglycidyl ether, novolak type epoxy and urethane polymer.

Figure 7:
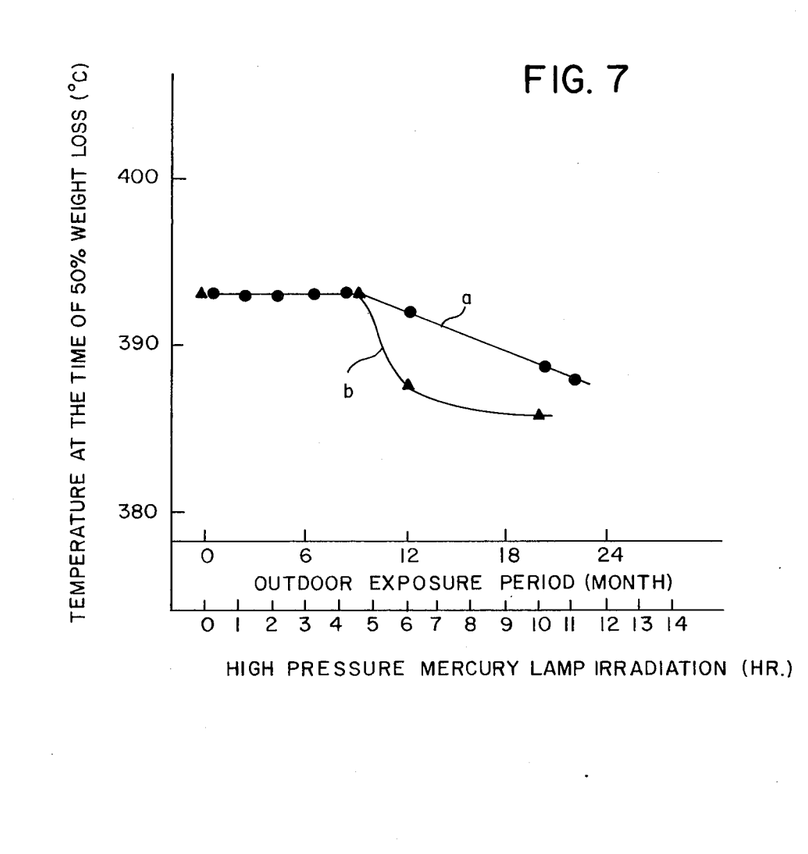

Results obtained are shown in FIG. 7. Curves a and b correspond to each other.

EXAMPLE 6

Figure 8:
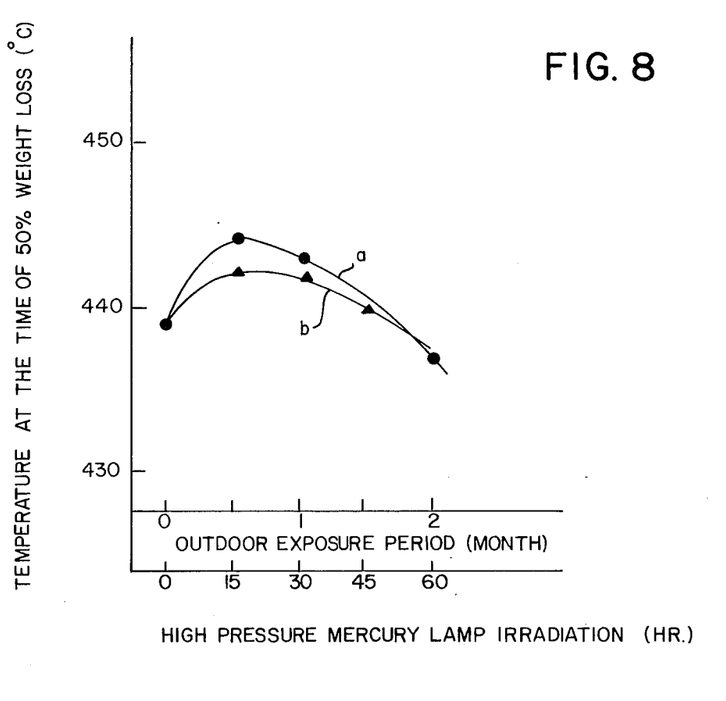

The film used was a biaxially-oriented film of a high impact polystyrene. Results are shown in FIG. 8. Curves a and b correspond to each other.

As the results of Examples 1, 3 and 4 (FIGS. 3, 5 and 6) show, the peak positions of curves a and b are found to nearly correspond to the whitening of the film. Unlike the polymers which produce the peaked curves shown in FIGS. 3 to 8, there exist polymer substances in which no peak is present when plotting the relation of the temperature at the time of 50% weight loss and the high pressure mercury lamp irradiation time. However, it is clear that upon whitening one can find a reduction corresponding to a peak for these polymer substances. An example of such a polymer substance is polymethyl methacrylate as shown in the following Example.

EXAMPLE 7

Figure 9:
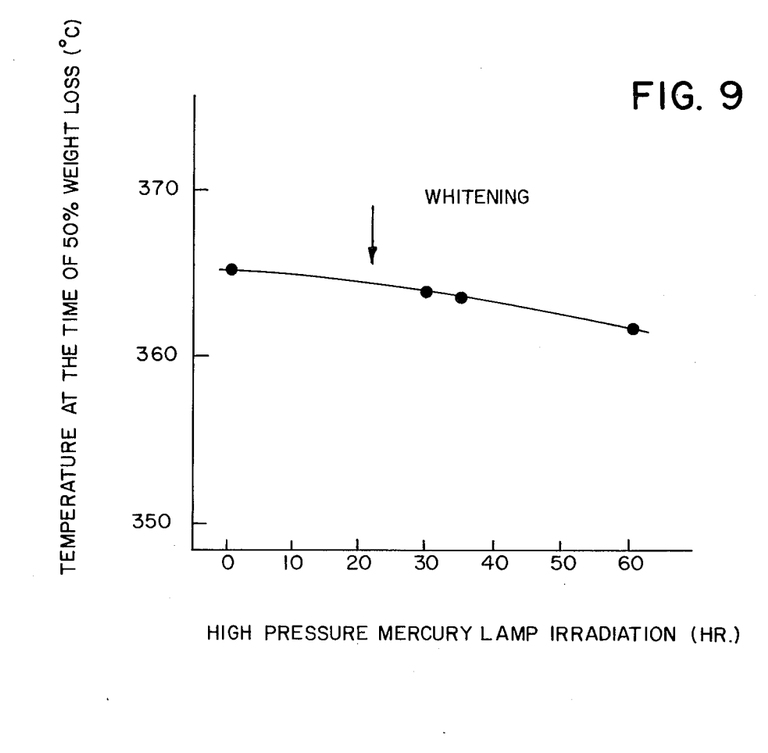

The film used was a film of a polymethyl methacrylate. Results are shown in FIG. 9. In this case, no peak was present, but whitening occurred at the time of irradiation for 20 hours (high pressure mercury lamp).

EXAMPLES 8–10

Figure 10:
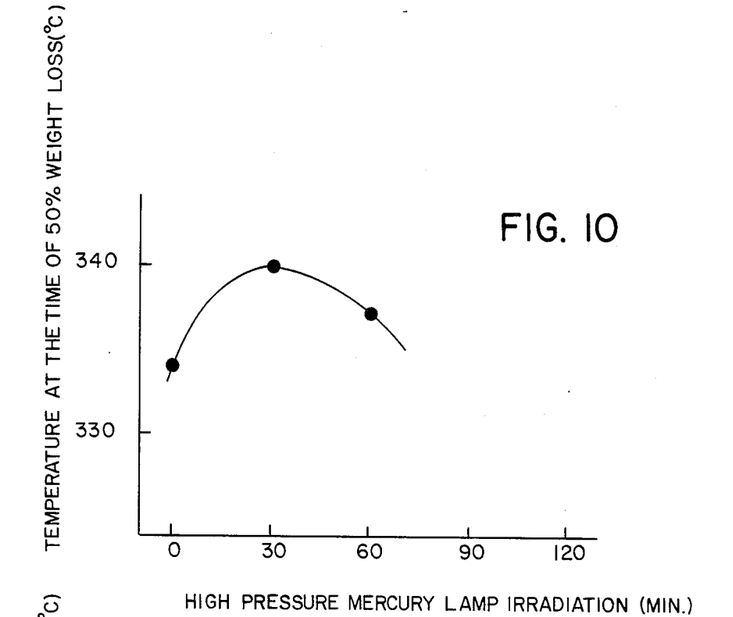
Figure 11:
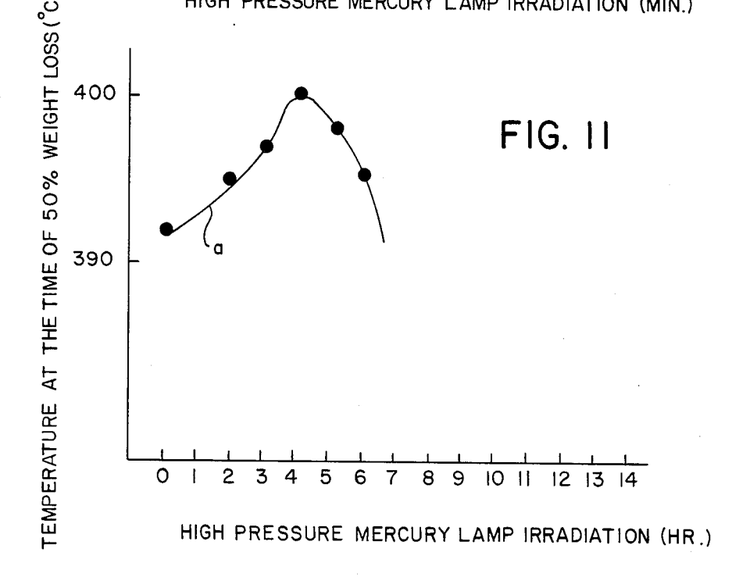
Figure 12:
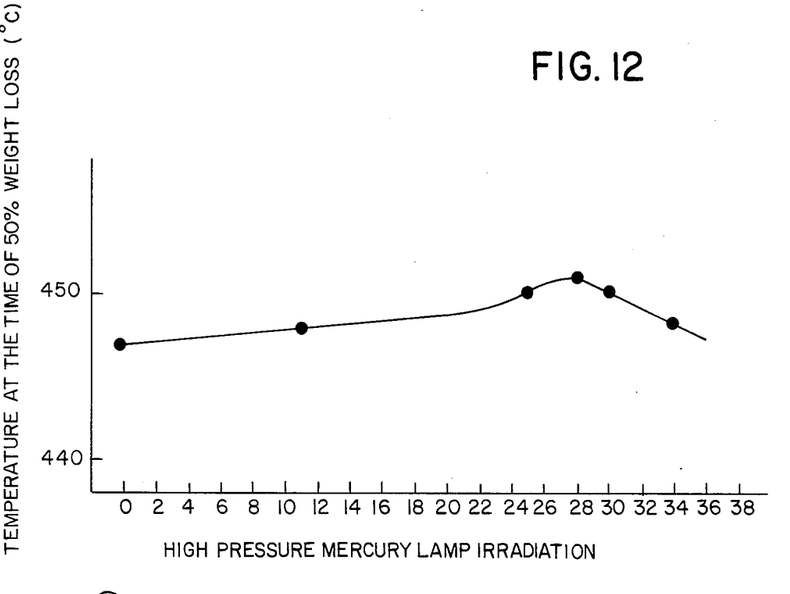

FIGS. 10, 11 and 12 show results obtained when using, as the polymer substance film, respectively a polyvinyl chloride film, a film of a blend of an epoxy resin (epichlorohydrin, bisphenol A) and polyurethane, and a film of HEVA type polyurethane (using, as polyol, a partial hydrolyzed product of an ethylene-vinyl acetate copolymer, which was crosslinked with IPDI).

In each of these cases, peaks are present.

EXAMPLE 11

Apart from the polymer substances indicated in the Examples 1–10, the process of the present invention was shown to be feasible for more general purpose resins, such as polyethylene, polypropylene, polycaprolactam, polyethylene terephthalate and polyacrylonitrile.

As illustrated by way of the above Examples, the present invention is advantageous in that it is capable of accelerating degradation of a polymer substance, determining the life of the polymer substance by natural degradation and simulating the life of the polymer substance in a very short period of time.

Figure 13:
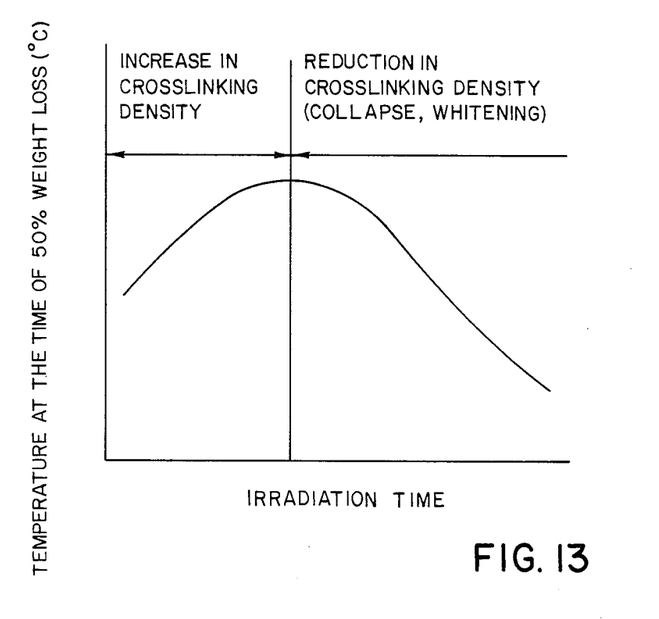
FIG. 13 is a schematic diagram which explains the results of FIGS. 3-12.

The instant inventors' study shows that by the practice of the process of the present invention the movement from an increase in crosslink density to a reduction (collapse) in crosslink density caused in the polymer substance can clearly be observed as a graph peak or by whitening due to the above treatment. This is indicated in the schematic diagram of FIG. 13.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A process for the acceleration of photodegradation of a polymer substance which comprises:
   (1) irradiating a polymer substance for a first predetermined time period with a first low wavelength light having a bright line or continuous spectral peak with a maximum intensity in a wavelength region of 400 nm or less; and then
   (2) irradiating said polymer substance for a second predetermined time period with a second high wavelength light having a bright line or continuous spectral peak with a maximum intensity on a wavelength region exceeding 400 nm, said process being conducted in an atmosphere with a water content of at least 0.034 g/l, whereby photodegradation of said polymer substance is accelerated.

2. A process according to claim 1, wherein said polymer substance is irradiated with said low wavelength light at a dose of about 30 to 100 milliwatts in bright line or peak with a wavelength of 250 nm per cm$^2$ of the surface area of said polymer substance.

3. A process according to claim 1, wherein said polymer substance is irradiated with said low wavelength light at a dose rate of about 1.8 to 6 watts·minutes per cm$^2$ of the surface areas of the polymer substance.

4. A process according to claim 1, wherein said polymer substance is irradiated with said low wavelength light for about 10 to 200 minutes.

5. A process according to claim 1, wherein said polymer substance is irradiated with said low wavelength light in an ambient atmosphere.

6. A process according to claim 1, wherein said low wavelength light irradiates from a low pressure mercury lamp which contains about 50 mmHg or less of mercury vapor pressure of enclosed mercury.

7. A process according to claim 1, wherein said low wavelength light irradiates from a source located at a distance of about 100 cm or less from said polymer substance.

8. A process according to claim 1, wherein said polymer substance is irradiated with said high wavelength light at a dose of about 0.5 to 4 watts in bright line or peak with a wavelength of 420 nm per cm$^2$ of the surface area of said polymer substance.

9. A process according to claim 1, wherein said polymer substance is irradiated with said high wavelength light at a dose rate of about 30 to 240 watts·minutes per cm$^2$ of the surface area of said polymer substance.

10. A process according to claim 1, wherein said polymer substance is irradiated with said high wavelength light for about 10 minutes to 100 hours.

11. A process according to claim 1, wherein said polymer substance is irradiated with said high wavelength light in an atmosphere with a water content of a least 0.038 g/l.

12. A process according to claim 1, wherein said high wavelength light irradiates from a high pressure or ultra-high pressure mercury lamp which is 1 to 20 atm. in mercury vapor pressure of enclosed mercury.

13. A process according to claim 1, wherein said high wavelength light irradiates from a source located at a distance of about 100 cm or less from said polymer substance.

14. A process according to claim 1, wherein said polymer substance is in the form of a thin film.

15. A process according to claim 14, wherein said thin film has a thickness of about 5 mm or less.

16. A process according to claim 1 wherein said polymer substance is selected from the group consisting of polyether polyurethane, epoxy resins, styrene-butadiene rubber, polyester-polyether polyurethane, polyether urethane, epoxy urethanic resins, polystyrene, polymethyl methacrylate, polyvinyl chloride, polyethylene, polypropylene, polycaprolactam, polyethylene terephthalate and polyacrylonitrile.

17. A process for determining the degradation life of a polymer substance which comprises:
   (1) irradiating a polymer substance for a first predetermined time period with a first low wavelength light having a bright line or continuous spectral peak with a maximum intensity in a wavelength region of 400 nm or less; and then
   (2) irradiating said polymer substance for a second predetermined time period with a second high wavelength light having a bright line or continuous spectral peak with a maximum intensity in a wavelength region exceeding 400 nm, wherein said polymer substance is irradiated in an atmosphere with a water content of at least 0.034 g/l, and
   (3) determining weight loss temperatures corresponding to weight loss values based on the proportion of weight loss of said polymer substance according to a thermogravimetric method wherein the weight loss is between 5 weight % and 95 weight % and comparing said weight loss temperatures to said second time period for irradiating said high wavelength light in order to determine temperature-time comparisons, and
   (4) determining the degradation life of said polymer substance based on said temperature-time comparisons.

18. A process according to claim 17, wherein the proportion of weight loss according to the thermogravimetric method is between 30 weight % and 70 weight %.

19. A process according to claim 17, wherein the proportion of weight loss according to the thermogravimetric method is 50 weight %.

20. A process according to claim 17, wherein said temperature-time comparisons are plotted as a curve with a peak and the degradation life of said polymer substance is determined by said peak.

21. An apparatus for accelerating the photodegradation of a polymer substance which comprises:
   a photodegradation compartment means;
   a lamp receiver means contained within said compartment means which receives an irradiation lamp means for irradiating a polymer substance sample, wherein said lamp receiver means is capable of having a coolant passed through it;
   a mounting plate means disposed opposite said lamp receiver means in said compartment means, wherein said mounting plate means is operatively connected to a drive motor means for rotating said mounting plate means and wherein said mounting plate means supports said polymer substance sample;
   humidifying means disposed within said compartment means for creating a predetermined humidity within said compartment means, said humidifying means including a humidifying cloth; and
   cooling means operatively associated with said lamp receiver means for passing aqueous coolant through said lamp receiver means at a predetermined temperature, wherein said cooling means comprises a coolant container for maintaining said aqueous coolant at a predetermined temperature and a circulating pump operatively connected to said coolant container and said lamp receiver means for pumping said aqueous coolant into said lamp receiver means from said coolant container.

* * * * *